(12) United States Patent
Kolter et al.

(10) Patent No.: US 9,789,065 B2
(45) Date of Patent: Oct. 17, 2017

(54) PROCESS FOR PRODUCING ORAL DOSAGE FORMS WITH CONTROLLED RELEASE

(75) Inventors: Karl Kolter, Limburgerhof (DE); Angelika Maschke, Mannheim (DE)

(73) Assignee: BASF SE, Ludwigshafen (DE)

(*) Notice: Subject to any disclaimer, the term of this patent is extended or adjusted under 35 U.S.C. 154(b) by 1277 days.

(21) Appl. No.: 13/122,827

(22) PCT Filed: Oct. 2, 2009

(86) PCT No.: PCT/EP2009/062800
§ 371 (c)(1),
(2), (4) Date: Apr. 6, 2011

(87) PCT Pub. No.: WO2010/040686
PCT Pub. Date: Apr. 15, 2010

(65) Prior Publication Data
US 2011/0195118 A1    Aug. 11, 2011

(30) Foreign Application Priority Data
Oct. 7, 2008   (EP) .................................. 08166013

(51) Int. Cl.
*A61K 9/16*   (2006.01)
*A61K 9/20*   (2006.01)

(52) U.S. Cl.
CPC .......... *A61K 9/1694* (2013.01); *A61K 9/1635* (2013.01); *A61K 9/2027* (2013.01)

(58) Field of Classification Search
CPC ... A61K 9/1694; A61K 9/1635; A61K 9/2027
See application file for complete search history.

(56) References Cited

U.S. PATENT DOCUMENTS

| | | | |
|---|---|---|---|
| 4,801,460 A | 1/1989 | Goertz et al. | |
| 7,413,750 B2 * | 8/2008 | Kolter et al. | 424/469 |
| 2001/0006677 A1 * | 7/2001 | McGinity et al. | 424/449 |
| 2001/0038852 A1 * | 11/2001 | Kolter et al. | 424/465 |
| 2007/0196500 A1 * | 8/2007 | Woo et al. | 424/490 |
| 2011/0195118 A1 | 8/2011 | Kolter et al. | |

FOREIGN PATENT DOCUMENTS

| | | |
|---|---|---|
| DE | 3612212 | 4/1986 |
| EP | 1166776 | 5/2001 |
| EP | 1138321 | 10/2001 |
| WO | 2008/080773 | 7/2008 |
| WO | 2010/040686 | 4/2010 |

OTHER PUBLICATIONS

Anonymous, "Placement of additives into a fluid stream", Apr. 1, 2003, Mason Publications, vol. 468, No. 113, XP00713255, pp. 623-639.*
Llinas et al., "Diclofenac Solubility: Independent Determination of the Intrinsic Solubility of Three Crystal Forms", Feb. 14, 2007, Journal of Medicinal Chemistry, vol. 50, No. 5, pp. 979-983.*
Kolter et al., "Kollicoat SR 30 D: A new sustained release excipient", Nov. 1999, BASF ExAct, No. 3, pp. 2-3.*
IPRP & Written Opinion in PCT/EP2009/062800, mailed Apr. 12, 2011, 9 pgs.
Anonymous, "Placement of additives into a fluid stream", *Mason Publications*, vol. 468, No. 113 Research Disclosure, XP00713255 Apr. 1, 2003, 17 pgs.

* cited by examiner

*Primary Examiner* — Michael B Pallay
(74) *Attorney, Agent, or Firm* — Servilla Whitney LLC

(57) ABSTRACT

A process for producing solid oral dosage forms with controlled active ingredient release, comprising a mixture of
a) at least one active ingredient, and
b) a preformulated mixture of polyvinyl acetate and polyvinylpyrrolidone,
wherein the mixture is obtained by joint processing of components a) and b) in an extruder at temperatures between 50° and 200° C.

1 Claim, 3 Drawing Sheets

PROCESS FOR PRODUCING ORAL DOSAGE FORMS WITH CONTROLLED RELEASE

CROSS-REFERENCE TO RELATED APPLICATIONS

This application is the National Stage entry of PCT/EP2009/062800, filed on Oct. 2, 2009, which claims priority to European Application Number 08166013.6, filed on Oct. 7, 2008.

Technical Field

The present invention relates to a process for producing solid oral dosage forms with controlled active ingredient release, comprising at least one active ingredient, a preformulated mixture of polyvinyl acetate and polyvinylpyrrolidone, optionally water-soluble polymers or lipophilic additives, and optionally further conventional excipients, wherein the processing of this mixture or parts of this mixture takes place in an extruder at temperatures between 60° and 200° C.

BACKGROUND

So-called depot or slow-release pharmaceutical forms with controlled release are becoming increasingly important in pharmaceutical therapy as a result of an improved, longer-lasting therapeutic effect and the fact that the dosage form needs to be administered less frequently. Besides the coated slow-release forms where the release is controlled by a coating, the usage of matrix forms in which the active ingredient is present embedded in a base from which it slowly diffuses out on contact with gastric or intestinal juice is becoming more frequent. These forms can be produced by various technologies such as, for example, direct tableting or wet granulation. The matrix formers frequently employed are erodable substances or gel formers such as hydroxypropylmethylcellulose or xanthan, which control the release on contact with aqueous media.

Disadvantages of these products and processes is that the release depends greatly on the mode of granulation, the particle size of the starting materials and granule particles, the compressive force and on the salt content or on the osmolarity of the release medium. There are often variations in release from tablet to tablet and from batch to batch. In addition, such tablets frequently exhibit insufficient mechanical stability, meaning a low resistance to crushing and a high friability.

EP-A 1166776 describes a process for producing oral dosage forms with a release-slowing effect, in which a preformulated mixture of polyvinyl acetate and polyvinylpyrrolidone is granulated with active ingredients by heating to 40-130° C. The granulation is brought about by softening the polyvinyl acetate to give a tacky material, and thus the powder particles cohere to give granule particles. The results achieved therewith in terms of the release of the active ingredient and the mechanical stability of the dosage form were reasonably good. Nevertheless, the granules obtained in this way exhibit certain disadvantages, for example in terms of the granule size and the porosity of the granule particles formed, which influence the release. The process becomes more difficult to control thereby.

EP-A 1138321 likewise describes tablets from a preformulated mixture of polyvinyl acetate and polyvinylpyrrolidone which are produced by direct tableting of physical powder mixtures or conventional granulation techniques and which likewise exhibit the disadvantages mentioned.

SUMMARY

It was an object of this invention to find a process with which these disadvantages are avoided and which consequently leads to very reproducible releases and mechanically very stable dosage forms. It was additionally intended to be simple and very reproducible to carry out.

The object has been achieved according to the invention by a process for producing solid oral dosage forms with controlled active ingredient release, comprising a mixture of
 a) at least one active ingredient,
 b) a preformulated mixture of polyvinyl acetate and polyvinylpyrrolidone,
wherein the mixture of components a) and b) takes place by joint processing of a) and b) in an extruder at temperatures between 50° and 200° C.

The extrusion takes place under a pressure of from 2 to 25 MPa, preferably 3 to 20 MPa, particularly preferably 5 to 15 MPa.

The porosity of the extruded mixture is less than 10% by volume, preferably less than 5% by volume, particularly preferably less than 1% by volume.

It is further possible to employ as components c), if appropriate, water-soluble polymers or lipophilic additives. Further conventional excipients can be employed, if appropriate, as components d). These components c) and/or d) are likewise incorporated in mixture with components a) and b) in the extruder.

DETAILED DESCRIPTION

Figure 1:
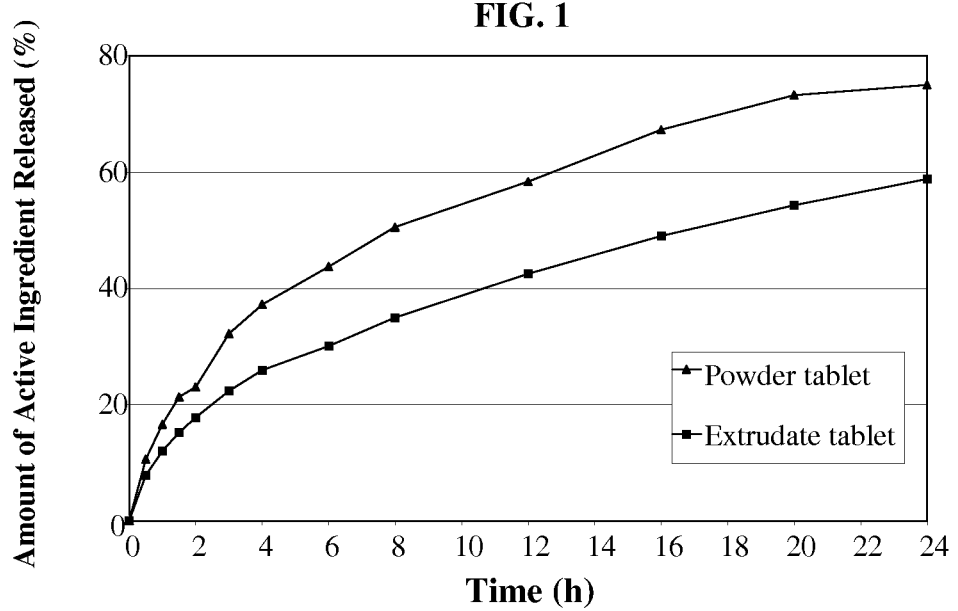
FIG. 1 is a graph of amount of active ingredient released (%) versus time (hours)

Controlled release in the context of the present invention means in particular a slowed release (also referred to as sustained release). According to the invention, less than 80% of the active ingredient is released in three hours.

The total of the amounts of a), b) and, optionally, c) and d) is 100% by weight.

It is possible to employ as component a) in principle any active ingredient which can be processed stably under the conditions of the process. The processed active ingredients are in particular those for which a sustained release is desired. The amounts in which the active ingredient is employed depends on the pharmaceutically relevant dosage of the active ingredient.

The following examples may be mentioned here:
benzodiazepines, antihypertensives, vitamins, cytostatics, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents and other antihyperkinetics, ophthalmologicals, neuropathy products, calcium metabolism regulators, muscle relaxants, narcotics, lipid-lowering agents, liver therapeutics, coronary agents, cardiac agents, immunotherapeutics, regulatory peptides and their inhibitors, hypnotics, sedatives, gynecologicals, antigout agents, fibrinolytics, enzyme products and transport proteins, enzyme inhibitors, emetics, perfusion promoters, diuretics, diagnostics, corticoids, cholinergics, biliary therapeutics, antiasthmatics, bronchospasmolytics, beta-receptor blockers, calcium channel blockers, ACE inhibitors, arteriosclerosis remedies, antiinflammatory agents, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, weight-reduction agents.

The process is particularly suitable for active ingredients with a solubility in water at 25° C. of less than 20 mg/ml, in particular less than 10 mg/ml. However, active ingredients with a better solubility in water, for example up to 100 mg/ml, can also be processed with the aid of the process of the invention.

A preformulated mixture of polyvinyl acetate and polyvinylpyrrolidone is employed as component b), in which polyvinyl acetate and polyvinylpyrrolidone are present in a ratio of from 6:4 to 9:1, preferably in the region of 8:2, by weight. At least 20% by weight of component b), based on the total amount of the extrudate, is employed in the extrudates. It may be up to 99.9% by weight, depending on the dosage of the active ingredient.

A homopolymer of vinyl acetate with a is referred to as polyvinyl acetate according to the invention. The polyvinyl acetates may have molecular weights of from 20000 to 1000000, preferably a molecular weight of 450000, daltons. A homopolymer of N-vinylpyrrolidone, in particular a polyvinylpyrrolidine with a Fikentscher K value of 30, is referred to as polyvinylpyrrolidone according to the invention. Suitable preformulated mixtures of polyvinyl acetate and polyvinylpyrrolidone K30 are commercially available as Kollidon® SR from BASF.

The preformulated mixture of polyvinyl acetate and polyvinylpyrrolidone can be obtained by dissolving polyvinylpyrrolidone in a fine-particle aqueous dispersion of polyvinyl acetate with a particle size of the polyvinyl acetate particles of from 100 to 300 nm, and subsequently spray drying the mixture obtained in this way. It may also be advisable to use a dusting agent such as, for example, silicon dioxide during the spray drying. To ensure that the two polymers do not mix in water or also during the spray drying, they are present in the form of a two-phase system that does not represent a physical mixture and could not be separated without destroying the structure.

The polyvinyl acetate dispersions used to produce the preformulated mixture may, besides the polyvinyl acetate, also comprise protective colloids to stabilize the aqueous dispersion, for example polyvinyl alcohol, polyvinylpyrrolidone, sodium lauryl sulfate or mixtures thereof. Suitable fine-particle aqueous polyvinyl acetate dispersions for producing the preformulated mixture are commercially available, for example as Kollicoat® SR30D from BASF, an aqueous dispersion with a solids content of 30% by weight, which comprises 27% by weight of polyvinyl acetate, 2.7% by weight of polyvinylpyrrolidone K30 and 0.3% by weight of sodium lauryl sulfate, based on the total weight of the dispersion.

Water-soluble polymers or lipophilic additives can be added as components c). Active ingredient release can be accelerated by adding low-viscosity, non-swelling water-soluble polymers such as polyvinyl alcohols, polyethylene glycols, polyoxyethylene-polyoxypropylene block polymers, polyvinylpyrrolidones, and copolymers of N-vinylpyrrolidone, for example vinyl acetate-vinylpyrrolidone copolymers, or starch derivatives, preferably polyethylene glycols, polyvinylpyrrolidones, vinyl acetate-vinylpyrrolidone copolymers or maltodextrins or mixtures thereof.

The release can be varied further by adding water-soluble, but swelling polymers as components c). Water-soluble swelling polymers which can be employed are: alginates, pectins, galactomannans, carrageenans, dextran, curdlan, pullulan, gellan, chitin, gelatin, xanthans, hemicelluloses, cellulose derivatives such as methylcellulose, hydroxypropylmethylcellulose, hydroxypropylcellulose, hydroxyethylcellulose, carboxymethylcellulose, starch derivatives such as carboxymethyl starch, polyacrylic acid, polymethacrylic acid, acrylic acid-methacrylic acid copolymers, polyvinyl alcohols, high molecular weight polyethylene glycols, polyoxyethylene-polyoxypropylene block polymers, and high molecular weight polyvinylpyrrolidones or mixtures of the substances mentioned.

An enhancement of the release-slowing effect can also be achieved by lipophilic additives as components c). It is important for these substances to be employed in small particle size because they display only a small, or no, effect in coarse form. Both polymers and low molecular weight compounds can be used as lipophilic additives. The polymers are, however, preferred. These additives include: cellulose derivatives such as ethylcellulose, cellulose acetate, cellulose acetate phthalate, cellulose acetate succinate, hydroxypropylmethylcellulose acetate phthalate, hydroxypropylmethylcellulose acetate succinate, acrylate ester-methacrylate ester copolymers, especially methyl methacrylate-ethyl acrylate copolymers, ammoniomethacrylate copolymer type A and type B, methacrylic acid-acrylic ester copolymers, in particular methacrylic acid-ethyl acrylate copolymers, fatty alcohols such as stearyl alcohol, fatty acids such as stearic acid, fatty acid esters and fatty alcohol esters, glycerides, waxes, lecithin.

The optional components c) can be employed in concentrations of from 1 to 40%, preferably from 2 to 30%, based on the total tablet weight. This is advantageous with very low-dose active ingredients, where the amount of formulated mixture of polyvinyl acetate and polyvinylpyrrolidone required to build up the structure might entail the release being slowed too much. This is further the case also with slightly soluble active ingredients, where although small amounts of release-slowing agent lead to delayed release, the structure is not completely built up and is subject to wide variations, and the mechanical stability of the tablets is inadequate. This is especially the case when the compressibility of the active ingredient is poor.

Conventional pharmaceutical excipients can optionally be included as components d) in the processing. These are substances from the class of fillers, plasticizers, solubilizers, binders, silicates, and disintegrants and adsorbents, lubricants, flowability agents, dyes, stabilizers such as antioxidants, wetting agents, preservatives, mold release agents, flavorings or sweeteners, preferably fillers, plasticizers and solubilizers.

Examples of fillers which can be added are inorganic fillers such as oxides of magnesium, aluminum, silicon, titanium carbonate or calcium carbonate, calcium phosphates or magnesium phosphates or organic fillers such as lactose, sucrose, sorbitol, mannitol.

Examples of suitable plasticizers are triacetin, triethyl citrate, glycerol monostearate, low molecular weight polyethylene glycols or poloxamers.

Suitable solubilizers are surface-active substances with an HLB (HydrophilicLipophilicBalance) greater than 11, for example hydrogenated castor oil ethoxylated with 40 ethylene oxide units (Cremophor® RH 40), castor oil ethoxylated with 35 ethylene oxide units (Cremophor eL), polysorbate 80, poloxamers or sodium lauryl sulfate.

Lubricants which can be used are stearates of aluminum, calcium, magnesium and tin, and magnesium silicate, silicones and the like.

Examples of flowability agents which can be employed are talc or colloidal silicon dioxide.

An example of a suitable binder is microcrystalline cellulose.

Disintegrants may be crosslinked polyvinylpyrrolidone or crosslinked sodium carboxymethyl starch. Stabilizers may be ascorbic acid or tocopherol.

Examples of dyes are iron oxides, titanium dioxide, triphenylmethane dyes, azo dyes, quinoline dyes, indigotine dyes, carotenoids, for coloring the dosage forms, opacifying agents such as titanium diodide or talc, in order to increase the transparency to light and to save on dyes.

Component b) is processed together with at least one active ingredient and, if desired, components c) and d) at elevated temperatures in the extruder. In this connection, material to be extruded is adjusted to temperatures of from 60 to 200° C., preferably 80 to 180° C., particularly preferably 100 to 150° C.

The process of the invention makes it possible to employ as extruders single-screw machines, intermeshing screw machines or else multiscrew extruders, especially twin screw extruders, corotating or counter rotating and, if appropriate, equipped with kneading disks. If it is desired to evaporate a solvent during the extrusion, the extruders are generally equipped with an evaporating section. The extruders are preferably further equipped with a venting device. The extruders may be equipped with a feed device for powdered or liquid starting materials. Twin screw extruders are particularly preferred.

Discharge from the extruder can take place through dies or die plates or breaker plates, with preference for discharge through dies. The dies may also be heatable.

The preparation of the invention leaves the extruder in the form of a strand or ribbon and can be broken down by means of a downstream calender into single-dose shaped articles. These may have a circular, oblong or football shape. Shaping to solid dosage forms by means of injection molding is also possible.

It is also possible to break down the strand by means of hot cut, underwater pelletization or water-cooled die face pelletization into pellets or granule particles which can be further processed in a pharmaceutically conventional way. For example, they can, with or without further conventional excipients, be packed into capsules or compressed to tablets. Previous grinding is also possible.

In a particular embodiment of the invention, instead of a strand a film with a layer thickness of 100-1000 μm is extruded, from which smaller pieces can be cut thereafter. These can be employed as so-called oral strips.

Owing to the high temperature and the high pressure in the extruder, the active ingredient is intimately mixed with the polymer base, so that the porosity is very low. The fact that virtually no air inclusions able to alter the structure of the formulation are present results on the one hand in a slower release than on conventional processing by melt granulation or direct tableting and a considerably more reproducible release. The melt granulation products disclosed in the abovementioned prior art are loose granules, i.e. structures composed of at least three phases: polymer, medicinal substance and air. The extrudates of the invention consist essentially only of two phases, specifically a polymer phase and active ingredient. The polyvinyl acetate is present as continuous phase in the polymer phase. Polyvinylpyrrolidone forms domains in the continuous PVAc phase.

In addition, the shaped articles are so hard but, at the same time, are so tough that they cannot be destroyed with the bare hands or even simple mechanical means such as a hammer. This prevents the abusive use of the tablets where the tablets are crushed and extracted in order to obtain the medicinal substance.

In this process, all of the medicinal substance or else only a certain part can be dissolved in the preformulated mixture of polyvinyl acetate and polyvinylpyrrolidone through the intimate mixing under pressure and high temperature, resulting in a solid solution. This explains inter alia the slow release and the better reproducibility. If all the medicinal substance dissolves in the preformulated mixture of polyvinyl acetate and polyvinylpyrrolidone, only one phase is present.

A great advantage of the process of the invention is further that it is possible to employ active ingredients differing greatly in particle size. This is not possible for example in direct tableting and melt granulation, because fine particles greatly reduce the flowability in direct tableting, and act as dusting agents on the larger polymer particles which have become tacky in the melt granulation, so that no granulation effect occurs. The process is particularly suitable for slightly soluble medicinal substances because they can be dissolved in the preformulated mixture of polyvinyl acetate and polyvinylpyrrolidone, so that the release no longer depends on the particulate state of the medicinal substance. When slightly soluble medicinal substances are in the particulate state, the particle size, the surface area, the wettability of the particle and the modification have a very great influence on the release.

EXAMPLES

Abbreviations Used:
PVAc: Polyvinyl acetate
PVP: Polyvinylpyrrolidone K30
VA 64: Kollidon® VA 64 (BASF), copolymer of N-vinylpyrrolidone and vinyl acetate in the ratio 6:4 by weight Unless stated otherwise, % data represent percentages by weight.

The suitability of extrusion for producing matrix sustained release tablets was investigated by using formulations with theophylline and the preformulated mixture of (0% by weight PVAc, 19% by weight PVP, 0.8% by weight sodium lauryl sulfate and 0.2% by weight silicon dioxide (Kollidon® SR) both with and without addition of VA 64 to control the release profile. The exact composition is indicated in table 1 below.

TABLE 1

| | Example No. | | | |
| --- | --- | --- | --- | --- |
| | 1 | 2 | 3 | 4 |
| Theophylline | 60% | 50% | 50% | 60% |
| Kollidon SR | 40% | 40% | 30% | 24% |
| VA64 | 0% | 10% | 20% | 16% |

A Werner & Pfleiderer ZSK 25 twin screw extruder was employed for the extrusion. The diameter of the screws was 25 mm, and the ratio of screw length to diameter was 34. The polymer-active ingredient melt was discharged through a die plate with three orifices with a diameter of 1.5 mm or 2 mm. In total, eight heatable elements were used.

The extrusion conditions and temperature profiles employed are listed in table 2.

TABLE 2

|  |  | Batch | | | |
| --- | --- | --- | --- | --- | --- |
|  |  | 1 | 2 | 3 | 4 |
| Melt pressure | [MPa] | 9.3 | 6.7 | 7.0 | 5.9 |
| Power | [kW] | 2.0 | 1.7 | 1.6 | 1.6 |
| Screw speed | [rpm] | 197 | 197 | 199 | 197 |
| Die diameter | [mm] | 2 | 2 | 1.5 | 2 |
| Number of dies |  | 3 | 2 | 3 | 2 |
| Torque | [A] | 10.3 | 8.4 | 8.1 | 8.0 |
| Heating zone 1 | [° C.] | 140 | 140 | 140 | 141 |
| Heating zone 2 | [° C.] | 139 | 139 | 138 | 140 |
| Heating zone 3 | [° C.] | 141 | 139 | 141 | 140 |
| Heating zone 4 | [° C.] | 142 | 139 | 140 | 138 |
| Heating zone 5 | [° C.] | 143 | 141 | 140 | 139 |
| Heating zone 6 | [° C.] | 137 | 144 | 141 | 143 |
| Heating zone 7 | [° C.] | 154 | 148 | 147 | 163 |
| Heating zone 8 | [° C.] | 151 | 148 | 150 | 157 |

The resulting extrudates were then ground and mixed with in each case 0.5 magnesium stearate. Tablets weighing 400 mg were produced using 12 mm beveled punches and a compressive force of 18 kN.

Tablets produced with ground extrudate powder tend to show a lower resistance to crushing and tensile strength. In terms of friability, the tablets correspond to those from direct tableting (see table 3).

TABLE 3

| | Batch | | | | | | | |
| --- | --- | --- | --- | --- | --- | --- | --- | --- |
| | 1 | | 2 | | 3 | | 4 | |
| Process | Powder | Extrudate | Powder | Extrudate | Powder | Extrudate | Powder | Extrudate |
| Resistance to Crushing [N] | 192 ± 24 | 196 ± 5 | 223 ± 8 | 175 ± 6 | 139 ± 5 | 107 ± 5 | 175 ± 6 | 139 ± 5 |
| Tensile strength [N/mm$^2$] | 3.5 ± 0.4 | 3.5 ± 0.1 | 3.9 ± 0.1 | 3.2 ± 0.1 | 2.5 ± 0.1 | 1.9 ± 0.1 | 3.2 ± 0.1 | 2.5 ± 0.1 |
| Friability [%] | 0.09 | 0.06 | 0.09 | 0.07 | 0.04 | 0.08 | 0.07 | 0.04 |

The influence of the extrusion on the release of active ingredient from the matrices is clearly evident from the release profiles of the batches. On use of 60% active ingredient and Kollidon SR, a distinctly slower release is achieved by extrusion (table 4 and FIG. 1)

TABLE 4

| | Example No. 1 Theophylline 60% Kollidon SR 40% VA64 0% | |
| --- | --- | --- |
| Time | Powder Release [%] | Extrudate Release [%] |
| 0.5 | 10.6 | 7.81 |
| 1 | 16.6 | 12.01 |
| 1.5 | 21.3 | 15.17 |
| 2 | 23.0 | 17.76 |
| 3 | 32.2 | 22.34 |

TABLE 4-continued

| | Example No. 1 Theophylline 60% Kollidon SR 40% VA64 0% | |
| --- | --- | --- |
| Time | Powder Release [%] | Extrudate Release [%] |
| 4 | 37.2 | 25.92 |
| 6 | 43.7 | 30.08 |
| 8 | 50.5 | 34.96 |
| 12 | 58.4 | 42.47 |
| 16 | 67.3 | 49.00 |
| 20 | 73.2 | 54.30 |
| 24 | 75.0 | 58.81 |

Figure 2:
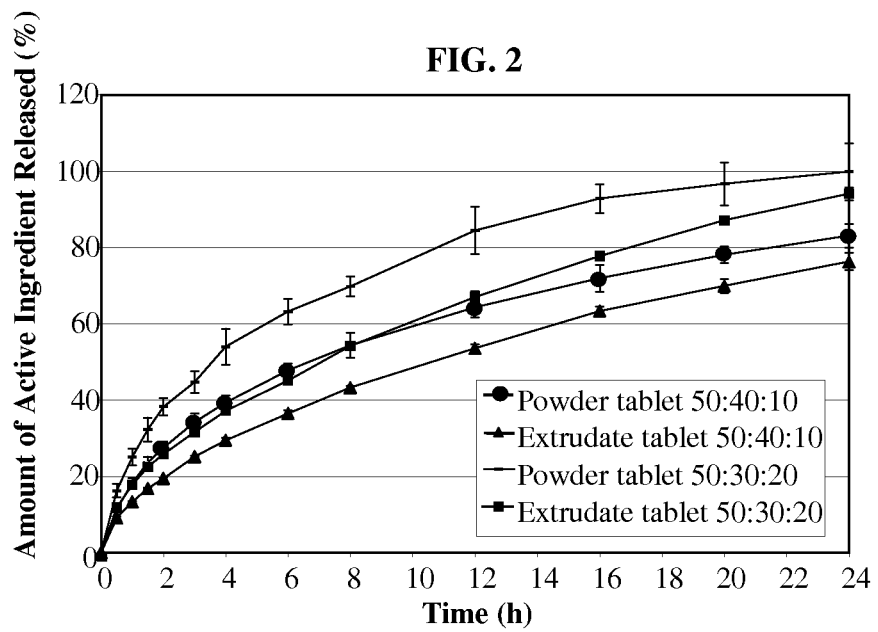
FIG. 2 is a graph of amount of active ingredient released (%) versus time (hours)

The release is accelerated by adding VA 64 to the formulation (see table 5 and FIG. 2). The extrudate tablets show a distinct slower and more uniform release.

TABLE 5

| | Active ingredient release | | | |
| --- | --- | --- | --- | --- |
| | Example No. | | | |
| | 2 Theophylline 50% Kollidon SR 40% VA64 10% | | 3 Theophylline 50% Kollidon SR 30% VA64 20% | |
| Time | Powder [%] | Extrudate [%] | Powder [%] | Extrudate [%] |
| 0.5 | 11.5 ± 0.3 | 9.1 ± 0.3 | 16.3 ± 1.8 | 11.8 ± 0.2 |
| 1 | 18.3 ± 1.2 | 13.3 ± 0.2 | 25.1 ± 2.2 | 17.9 ± 0.2 |
| 1.5 | 23.6 ± 1.5 | 16.8 ± 0.2 | 32.3 ± 3.1 | 22.5 ± 0.6 |
| 2 | 27.5 ± 1.6 | 19.4 ± 0.3 | 38.3 ± 2.2 | 25.9 ± 0.7 |
| 3 | 34.2 ± 2.3 | 25.2 ± 0.2 | 44.7 ± 2.8 | 31.6 ± 0.6 |
| 4 | 39.3 ± 1.9 | 29.5 ± 0.6 | 54.0 ± 4.8 | 37.2 ± 0.6 |
| 6 | 47.8 ± 1.8 | 36.5 ± 0.8 | 63.2 ± 3.3 | 45.1 ± 0.4 |
| 8 | 54.3 ± 3.3 | 43.3 ± 0.4 | 69.8 ± 2.6 | 54.2 ± 0.4 |

TABLE 5-continued

Active ingredient release

| | Example No. 2 Theophylline 50% Kollidon SR 40% VA64 10% | | Example No. 3 Theophylline 50% Kollidon SR 30% VA64 20% | |
|---|---|---|---|---|
| Time | Powder [%] | Extrudate [%] | Powder [%] | Extrudate [%] |
| 12 | 64.3 ± 2.6 | 53.6 ± 1.0 | 84.5 ± 6.1 | 67.1 ± 1.4 |
| 16 | 71.9 ± 3.5 | 63.4 ± 1.1 | 92.8 ± 3.7 | 77.8 ± 0.2 |
| 20 | 78.1 ± 2.2 | 69.9 ± 1.8 | 96.7 ± 5.6 | 87.1 ± 0.7 |
| 24 | 83.1 ± 3.0 | 76.3 ± 2.2 | 99.9 ± 7.5 | 94.1 ± 1.7 |

Figure 3:
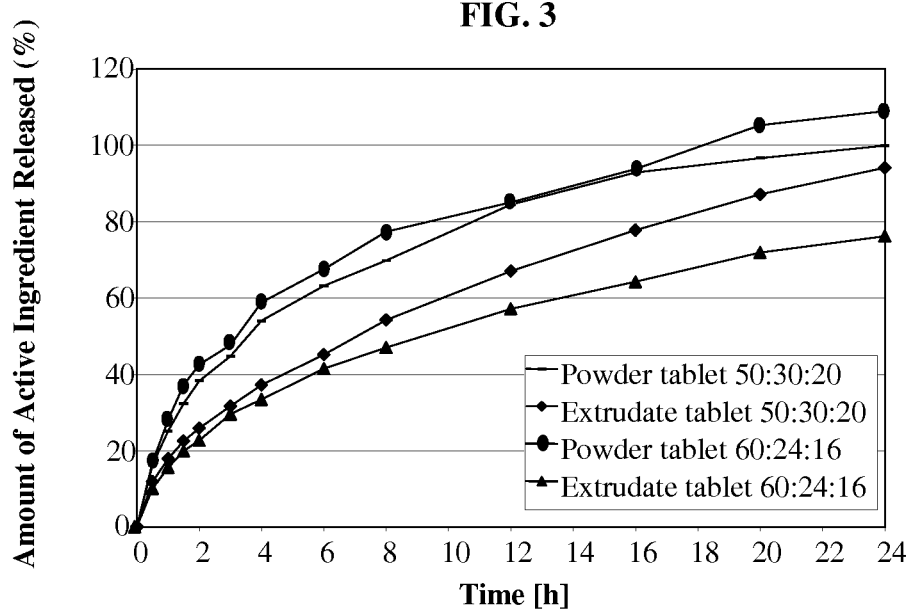
FIG. 3 is a graph of amount of active ingredient released (%) versus time (hours).

If the Kollidon SR: VA 64 ratio is kept constant, the extrudate tablets show a distinct slower and more uniform release with a smaller range of variation (table 6, FIG. 3). A further advantage of the extrudates is that there is no flattening of the curve after 50% release; on the contrary, it follows linear zero order kinetics. It is further possible to accelerate release by increasing the Kollidon VA 64 content, whereas virtually identical, fast release profiles are obtained with tablets produced by direct tableting of powder mixtures, and moreover show a wide range of variation.

TABLE 6

| | Theophylline 50% Kollidon SR 30% Kollidon VA64 20% | | Theophylline 60% Kollidon SR 24% Kollidon VA64 16% | |
|---|---|---|---|---|
| Time [h] | Powder [%] | Extrudate [%] | Powder [%] | Extrudate [%] |
| 0.5 | 16.3 | 11.8 | 17.0 | 10.0 |
| 1 | 25.1 | 17.9 | 28.1 | 15.5 |
| 1.5 | 32.3 | 22.5 | 37.2 | 19.9 |
| 2 | 38.3 | 25.9 | 42.5 | 22.7 |
| 3 | 44.7 | 31.6 | 47.7 | 29.5 |
| 4 | 54.0 | 37.2 | 58.8 | 33.4 |
| 6 | 63.2 | 45.1 | 67.6 | 41.5 |
| 8 | 69.8 | 54.2 | 77.3 | 47.0 |
| 12 | 84.5 | 67.1 | 85.1 | 57.2 |
| 16 | 92.8 | 77.8 | 93.8 | 64.2 |
| 20 | 96.7 | 87.1 | 105.3 | 71.9 |
| 24 | 99.9 | 94.1 | 108.9 | 76.2 |

We claim:

1. A process for producing solid oral dosage forms with controlled active ingredient release, comprising a mixture of:

a) at least one active ingredient, and b) a preformulated mixture of polyvinyl acetate and polyvinylpyrrolidone;

wherein the mixture is obtained by joint processing of components a) and b) in an extruder at temperatures between 80° and 180° C.; wherein said preformulated mixture is obtained by dissolving polyvinylpyrrolidone in a fine-particle aqueous dispersion of polyvinyl acetate with a particle size of the polyvinyl acetate particles of from 100 to 300 nm, and subsequently spray driving; and wherein extrusion takes place under a pressure of from 2 to 25 MPa;

wherein a film with a layer thickness of 100-1000 μm is extruded, from which small pieces of film for oral administration are cut out directly thereafter.

* * * * *